(12) United States Patent
Itakura et al.

(10) Patent No.: US 9,358,257 B2
(45) Date of Patent: Jun. 7, 2016

(54) USE OF CELL WALL DISRUPTED PRODUCT OF CHLORELLA FOR REDUCING SERUM RESISTIN LEVEL

(71) Applicant: SUN CHLORELLA CORP., Kyoto (JP)

(72) Inventors: Hiroshige Itakura, Tokyo (JP); Tetsuaki Nakayama, Kyoto (JP); Ryo Matoba, Kanagawa (JP)

(73) Assignee: SUN CHLORELLA CORP., Kyoto-shi, Kyoto (JP)

( * ) Notice: Subject to any disclaimer, the term of this patent is extended or adjusted under 35 U.S.C. 154(b) by 0 days.

(21) Appl. No.: 14/328,236

(22) Filed: Jul. 10, 2014

(65) Prior Publication Data

US 2014/0322261 A1    Oct. 30, 2014

Related U.S. Application Data

(63) Continuation-in-part of application No. PCT/JP2013/050341, filed on Jan. 10, 2013.

(30) Foreign Application Priority Data

Jan. 11, 2012  (JP) ................ 2012-002864

(51) Int. Cl.
*A61K 36/05*     (2006.01)
*A61K 35/66*     (2015.01)
*A23L 1/30*      (2006.01)
*A23L 1/337*     (2006.01)

(52) U.S. Cl.
CPC ........... *A61K 35/66* (2013.01); *A23L 1/3002* (2013.01); *A23L 1/337* (2013.01); *A61K 36/05* (2013.01)

(58) Field of Classification Search
CPC ..................................... A61K 36/05
USPC ..................................... 424/195.17
See application file for complete search history.

(56) References Cited

U.S. PATENT DOCUMENTS

| 2003/0008048 | A1* | 1/2003 | Winston et al. ............ 426/548 |
| 2004/0185063 | A1* | 9/2004 | Ray ........................... 424/195.17 |
| 2005/0196389 | A1* | 9/2005 | Dockery et al. .............. 424/94.1 |

FOREIGN PATENT DOCUMENTS

| CN | 101978974    | * | 2/2001 |
| JP | 2005-89322 A |   | 4/2005 |
| JP | 2005089322   | * | 4/2005 |
| JP | 2005089325   | * | 4/2005 |
| JP | 2005089326   | * | 4/2005 |
| JP | 2006069994   | * | 3/2006 |
| JP | 2008-231072 A |   | 10/2008 |
| JP | 2008231072   | * | 10/2008 |

OTHER PUBLICATIONS

Mojiminiyi OA, Abdella NA, Associations of resistin with inflammation and insulin resistance in patients with type 2 diabetes mellitus, Scand J Clin Lab Invest. 2007;67(2): pp. 215-225.

Tokuyama Y, Osawa H, Ishizuka T, Onuma H, Matsui K, Egashira T, Makino H, Kanatsuka A, Serum resistin level is associated with insulin sensitivity in Japanese patients with type 2 diabetes mellitus, Metabolism. May 2007;56(5): pp. 693-698.

Nagaev I, Bokarewa M, Tarkowski A, Smith U, Human resistin is a systemic immune-derived proinflammatory cytokine that targets both leukocytes and adipocytes, PLoS One. Dec. 20, 2006;1:e31.

Toru Mizoguchi et al., "Chlorella in'yo ni Tomonau Idenshi Hatsugen Kaiseki: Seikatsu Shukan Yobigun to Kenjoshagun no Hikaku Kento", The Japanese Society of Nutrition and Food Science Sokai Koen Yoshishu, Apr. 1, 2006, 60th, 381.

Toru Mizoguchi et al., "Effect of chlorella on the metabolic syndrome using spontaneous obese mice", Medicine and Biology, 153 (8), Aug. 10, 2009, 317-326.

* cited by examiner

*Primary Examiner* — Chris R Tate
(74) *Attorney, Agent, or Firm* — McGlew and Tuttle, P.C.

(57) ABSTRACT

A serum resistin level reducing agent that comprises a cell wall disrupted product of a *Chlorella pyrenoidos*, and that reduces a serum resistin level, as an agent for oral administration. A food or beverage composition for reducing a serum resistin level that comprises a cell wall disrupted product of a *Chlorella pyrenoidos*, and that reduces a serum resistin level. A method of reducing a serum resistin level by applying a cell wall disrupted product of a chlorella for oral administration. A use of a cell wall disrupted product of a chlorella for oral administration for reducing a serum resistin level.

5 Claims, 3 Drawing Sheets

USE OF CELL WALL DISRUPTED PRODUCT OF CHLORELLA FOR REDUCING SERUM RESISTIN LEVEL

CROSS REFERENCE TO RELATED APPLICATION

This is a continuation-in-part of and claims the benefit (35 U.S.C. §120 and 365(c)) of copending International Application PCT/JP2013/050341 filed Jan. 10, 2013, which designated inter alia the United States and which claims the priority of Japanese Patent Application JP 2012-002864 of Jan. 11, 2012. The entire contents of each application is hereby incorporated by reference in its entirety.

BACKGROUND OF THE INVENTION

1. Field of the Invention

The present invention relates to a serum resistin level reducing agent for reducing a serum resistin level and a food or beverage composition for reducing a serum resistin level, as well as a method for reducing a serum resistin level and a use for reducing a serum resistin level.

2. Description of the Prior Art

Sugar metabolism abnormalities and blood resistin levels correlate with each other [Scand J Clin Lab Invest. 2007; 67(2):215-25. Associations of resistin with inflammation and insulin resistance in patients with type 2 diabetes mellitus. Mojiminiyi O A, Abdella N A; Metabolism. 2007 May; 56(5): 693-8. Serum resistin level is associated with insulin sensitivity in Japanese patients with type 2 diabetes mellitus. Tokuyama Y, Osawa H, Ishizuka T, Onuma H, Matsui K, Egashira T, Makino H, Kanatsuka A], and resistin has been reported to act on adipocytes to induce inflammation of the adipocytes and increase cytokines that induce insulin resistance (PLoS One. 2006 Dec. 20; 1:e31. Human resistin is a systemic immune-derived proinflammatory cytokine that targets both leukocytes and adipocytes. Nagaev I, Bokarewa M, Tarkowski A, Smith U).

Therefore, there is a demand for a serum resistin level reducing agent and a food or beverage composition for reducing a serum resistin level, that are safe, suitable for oral administration, and capable of effectively reducing a blood resistin level, as well as a method for reducing a serum resistin level and a use for reducing a serum resistin level.

SUMMARY OF THE INVENTION

The present invention has been developed in view of the above, and is intended to provide a serum resistin level reducing agent and a food or beverage composition for reducing a serum resistin level, that can be safely and conveniently administered over a long period, as well as a method for reducing a serum resistin level and a use for reducing a serum resistin level that can be safely and conveniently performed over a long period.

One of the embodiment of the present invention there is provided a serum resistin level reducing agent comprises a cell wall disrupted product of a chlorella.

Another embodiment of the present invention there is provided a food or beverage composition for reducing a serum resistin level comprises a cell wall disrupted product of a chlorella.

Another embodiment of the present invention there is provided a method for lowering a serum resistin level by applying a cell wall disrupted product of a chlorella.

Another embodiment of the present invention there is provided a use of a cell wall disrupted product of a chlorella for lowering a serum resistin level.

By applying the serum resistin level reducing agent or food or beverage composition for reducing a serum resistin level of the present invention, or by using the method for reducing a serum resistin level or cell wall disrupted product of a chlorella of the present invention, a serum resistin level can be effectively reduced.

The serum resistin level reducing agent of the present invention may be such that it lowers the expression of the resistin gene.

The food or beverage composition for reducing a serum resistin level of the present invention may be such that it lowers the expression of the resistin gene.

The method for reducing a serum resistin level of the present invention may be such that it reduces the expression of the resistin gene.

The use of a cell wall disrupted product of a chlorella of the present invention may be for reducing the expression of the resistin gene.

The above-described serum resistin level reducing agent of the present invention may be such that it increases the expression of the CTBP1 gene.

The above-described food or beverage composition for reducing a serum resistin level of the present invention may be such that it increases the expression of the CTBP1 gene.

The method for reducing a serum resistin level of the present invention may be such that it increases the expression of the CTBP1 gene.

The use of a cell wall disrupted product of a chlorella of the present invention may be such that it increases the expression of the CTBP1 gene.

The CTBP1 gene negatively controls the expression of the resistin gene.

The above-described serum resistin level reducing agent of the present invention may be such that it increases the expression of the CTBP2 gene.

The above-described food or beverage composition for reducing a serum resistin level of the present invention may be such that it increases the expression of the CTBP2 gene.

The method for reducing a serum resistin level of the present invention may be such that it increases the expression of the CTBP2 gene.

The use of a cell wall disrupted product of a chlorella of the present invention may be such that it increases the expression of the CTBP2 gene.

The CTBP2 gene negatively controls the expression of the resistin gene.

The above-described serum resistin level reducing agent of the present invention may be such that it increases the expression of the RXR-alpha gene.

The above-described food or beverage composition for reducing a serum resistin level of the present invention may be such that it increases the expression of the RXR-alpha gene.

The method for reducing a serum resistin level of the present invention may be such that it increases the expression of the RXR-alpha gene.

The use of a cell wall disrupted product of a chlorella of the present invention may be such that it increases the expression of the RXR-alpha gene.

The RXR-alpha gene negatively controls the expression of the resistin gene.

The chlorella in the serum resistin level reducing agent of the present invention may be *Chlorella pyrenoidosa*.

The chlorella in the food or beverage composition for reducing a serum resistin level of the present invention may be *Chlorella pyrenoidosa*.

The chlorella in the method for reducing a serum resistin level of the present invention may be *Chlorella pyrenoidosa*.

The chlorella in the use of a cell wall disrupted product of a chlorella of the present invention may be *Chlorella pyrenoidosa*.

The serum resistin level reducing agent of the present invention may be an agent for oral administration.

In the method for reducing a serum resistin level of the present invention, a cell wall disrupted product of a chlorella may be applied by oral administration.

In the use of a cell wall disrupted product of a chlorella of the present invention, a cell wall disrupted product of a chlorella may be used for oral administration.

"A serum resistin level reducing agent" in the present invention may be reworded to "a substance for reducing a serum resistin level."

A method for reducing a serum resistin level by applying the serum resistin level reducing agent or food or beverage composition for reducing a serum resistin level of the present invention may be reworded to a method for reducing a serum resistin level by applying a cell wall disrupted product of a chlorella.

The serum resistin level reducing agent and food or beverage composition for reducing a serum resistin level of the present invention can be safely and conveniently administered over a long period to effectively reduce a serum resistin level. The method for reducing a serum resistin level and use for reducing a serum resistin level of the present invention can be safely and conveniently performed over a long period to effectively reduce a serum resistin level.

DETAILED DESCRIPTION OF THE INVENTION

Figure 1:
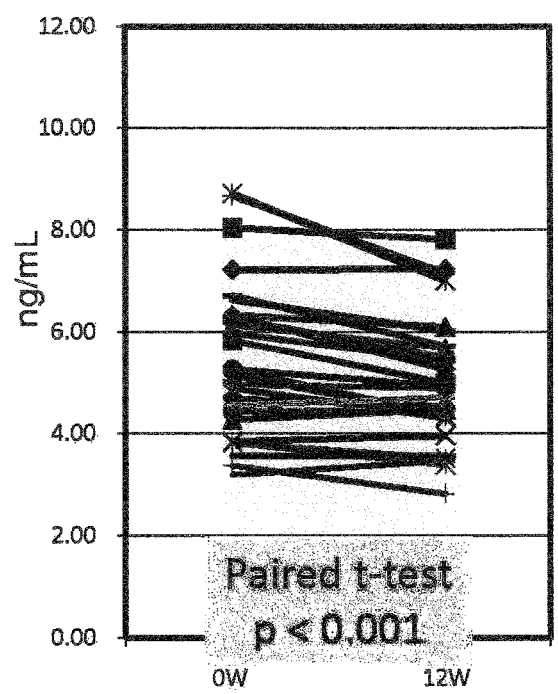
FIG. 1 is a results of measurement of serum resistin levels obtained before the test period (0 w) and after the end of the test period (12 w).

The chlorella in the present invention refers to a single-cell green alga belonging to the genus *Chlorella*, and is exemplified by *Chlorella pyrenoidosa*, *Chlorella ellipsoidea*, *Chlorella vulgaris*, and *Chlorella regularis*. The most suitable chlorella for the present invention is *Chlorella pyrenoidosa*.

The cell wall disrupted product of a chlorella in the serum resistin level reducing agent and food or beverage composition for reducing a serum resistin level of the present invention, as well as the method for reducing a serum resistin level and use thereof for reducing a serum resistin level of the present invention can, for example, be obtained as described below. Specifically, first, an aqueous suspension of chlorella powder having a chlorella concentration of 10 to 25% by weight is adjusted to a temperature of not more than 10 degrees Celsius. Subsequently, this suspension is fed to a continuous wet pulverizer as described below, and pulverized so that the temperature of the slurry just after disruption will not be more than 40 degrees Celsius. Subsequently, the chlorella slurry thus obtained is immediately cooled to a temperature of not more than 10 degrees Celsius, whereby a chlorella with a disrupted cell wall can be obtained without resulting in quality deterioration.

The above-described continuous wet pulverizer has a large number of glass beads 0.5 to 1.5 mm in diameter enclosed in a closed cylinder with a cooling jacket. The volume of the glass beads is 80 to 85% of the capacity of the closed cylinder, and the material in the influent liquid is ground by mixing and rotating the glass beads with the influent liquid.

The chlorella having a cell wall thus disrupted may be used as it is, and may also be used after being subjected to an appropriate treatment, for example, vacuum drying followed by milling.

The cell wall disrupted product of a chlorella in the serum resistin level reducing agent and food or beverage composition for reducing a serum resistin level of the present invention, as well as the method for reducing a serum resistin level and the use for reducing a serum resistin level of the present invention is suitable for oral administration. The dose of a cell wall disrupted product of *Chlorella pyrenoidosa* (or a cell wall disrupted product of any other chlorella) for an adult human is appropriately about 1 to 35 g per day. However, because cell wall disrupted product of *Chlorella pyrenoidosa* and the like are not toxic to the human body, this dose range is not construed as limiting the present invention.

Although the dosage form for oral administration in the serum resistin level reducing agent, method for reducing a serum resistin level, and use thereof for reducing a serum resistin level of the present invention is not subject to limitations, the dosage form can be prepared as, for example, powders, tablets, hard capsules, and soft capsules.

To form a wide variety of dosage forms, various excipients, binders, disintegrating agents, lubricants, coating agents, coloring agents, taste-masking agents, odor-masking agents, plasticizers, and the like may be used as appropriate.

Examples of excipients include saccharides (lactose, sucrose, glucose, mannitol), starches (potato, wheat, corn), inorganic substances (calcium carbonate, calcium sulfate, sodium hydrogen carbonate, sodium chloride), crystalline cellulose, powdered plants (powdered glycyrrhiza, powdered gentian), and the like.

Examples of binders include starch glue liquid, gum arabic, gelatin, sodium alginate, methyl cellulose (MC), ethyl cellulose (EC), polyvinylpyrrolidone (PVP), polyvinyl alcohol (PVA), hydroxypropyl cellulose (HPC), carboxymethyl cellulose (CMC), and the like.

Examples of disintegrating agents include starches, agar, powdered gelatin, crystalline cellulose, CMC-Na, CMC-Ca, calcium carbonate, sodium hydrogen carbonate, sodium alginate, and the like.

Examples of lubricants include magnesium stearate, talc, hydrogenated vegetable oils, macrogol, silicone oil, and the like.

Examples of coating agents include sugar coatings (sucrose, HPC, shellac), gelatin coatings (gelatin, glycerin, sorbitol), film coatings [hydroxypropylmethyl cellulose (HPMC), EC, HPC, PVP], enteric coatings [hydroxypropylmethyl cellulose phthalate (HPMCP), cellulose acetate phthalate (CAP)], and the like.

Examples of coloring agents include water-soluble food dyes, lake pigments, and the like. Examples of taste-masking agents include lactose, sucrose, glucose, mannitol, and the like. Examples of odor-masking agents include aromatic essential oils, light screens (titanium oxide), and the like.

Examples of plasticizers include phthalic acid esters, vegetable oils, polyethylene glycol, and the like.

The food or beverage composition for reducing a serum resistin level of the present invention can, for example, be prepared in the form of a food or beverage composition for nutritional food, nutritional supplement, liquid beverage, or the like, and that contains a cell wall disrupted product of a chlorella, and may contain various components that do not interfere with the effect of the present invention.

Such a serum resistin level reducing agent and food or beverage composition for reducing a serum resistin level can be safely and conveniently administered over a long period to effectively reduce a serum resistin level. Such a method for reducing a serum resistin level and use for reducing a serum resistin level can be safely and conveniently performed over a long period to effectively reduce a serum resistin level.

EXAMPLES

A test was performed to determine the effects of oral administration of a cell wall disrupted product of a chlorella on a serum resistin level, the expression of the resistin gene, and the expression of genes that negatively control the expression of the resistin gene.

1. Production of Test Substance

A dry powder of *Chlorella pyrenoidosa* with a disrupted cell wall as a test substance (hereinafter also simply referred to as "chlorella") was produced as described below.

An aqueous suspension of *Chlorella pyrenoidosa* powder having a *Chlorella pyrenoidosa* concentration of 10 to 25% by weight, previously adjusted to a temperature of not more than 10 degrees Celsius, was fed to a continuous wet pulverizer (product name: Dyno-Mill Model KD, manufactured by WAB, Inc.) that had a large number of glass beads 0.5 to 1.5 mm in diameter enclosed in a closed cylinder with a cooling jacket, in a volume 80 to 85% of the capacity of the closed cylinder, and that ground the material in the influent liquid by mixing and rotating the glass beads with the influent liquid, and pulverized so that the temperature of the slurry just after disruption would not be more than 40 degrees Celsius. Subsequently, the *Chlorella pyrenoidosa* slurry thus obtained was immediately cooled to a temperature of not more than 10 degrees Celsius, vacuum dried, and then milled, whereby dry powdered *Chlorella pyrenoidosa* with a disrupted cell wall (a chlorella powder with a disrupted cell wall, produced by SUN CHLORELLA Corporation), which served as the test substance, was obtained.

2. Test Method

The test substance, 3.83 g (7.66 g per day), was orally administered to each of 28 subjects (42- to 49-year-old males with an HbA1c level of not less than 5.3% and less than 6.1%) before breakfast and before dinner every day for 12 weeks (test period).

Peripheral blood was drawn before oral administration of the test substance on the first day of the test period (0 w) and before breakfast on the day after the end of the test period (12 w), and used as samples for measurement of serum resistin levels, the expression of the resistin gene, and the expression of genes that negatively control the expression of the resistin gene. Taking any food or beverage other than water was prohibited between 21:00 o'clock of the day before the first day of the test period and the time of blood drawing on the first day.

3. Measuring Methods (1) Resistin Levels

Each sample was analyzed for resistin by ELISA using a human resistin ELISA kit (product name: Human Resistin ELISA, manufactured by BioVendor Laboratorni medicina a.s.), and the absorbance from each well was measured using a microplate reader with a main wavelength of 450 nm and a secondary wavelength of 630 nm to determine the resistin level.

(2) Gene Expression

Total RNA was extracted from each sample in a vacuum blood drawing tube for RNA isolation (product name: PAXgene Blood RNA Tube, manufactured by BD) using an RNA extraction kit (product name: PAXgene Blood miRNA Kit, manufactured by QIAGEN).

The yield of the extracted total RNA was determined using a spectrophotometer (product name: NanoDrop 1000, manufactured by Thermo Scientific), and the degree of degradation was determined using an analyzer (product name: Agilent 2100 Bioanalyzer, manufactured by Agilent Technologies).

Microarray analysis was performed using a gene expression microarray (product name: SurePrint G3 Human GE 8×60K Microarray, manufactured by Agilent Technologies). Labeled cRNA was prepared from 100 ng of the total RNA using a gene expression microarray labeling kit (product name: Low Input Quick Amp Labeling Kit, manufactured by Agilent Technologies) in accordance with the standard protocol thereof. Labeling was achieved by the one-color method using Cyanine 3.

Microarray scans were performed using a microarray scanner (product name: G2505C DNA microarray scanner, manufactured by Agilent Technologies), and digitization was performed using microarray image digitizing software (product name: Feature Extraction Software ver. 10.7.3.1, manufactured by Agilent Technologies).

4. Results

Results of measurement of serum resistin levels, the expression of the resistin gene, and the expression of genes that negatively control the expression of the resistin gene obtained before the test period (0 w) and after the end of the test period (12 w) are as follows:

(1) Serum Resistin Levels

The results of measurement of serum resistin levels before the test period (0 w) and after the end of the test period (12 w) are shown in FIG. 1; the serum resistin level decreased significantly with oral administration of the test substance. The mean serum resistin level in the subjects was 5.47 ng/mL before the test period (0 w) and 5.02 ng/mL after the end of the test period (12 w).

(2) Expression of the Resistin Gene

Figure 2:
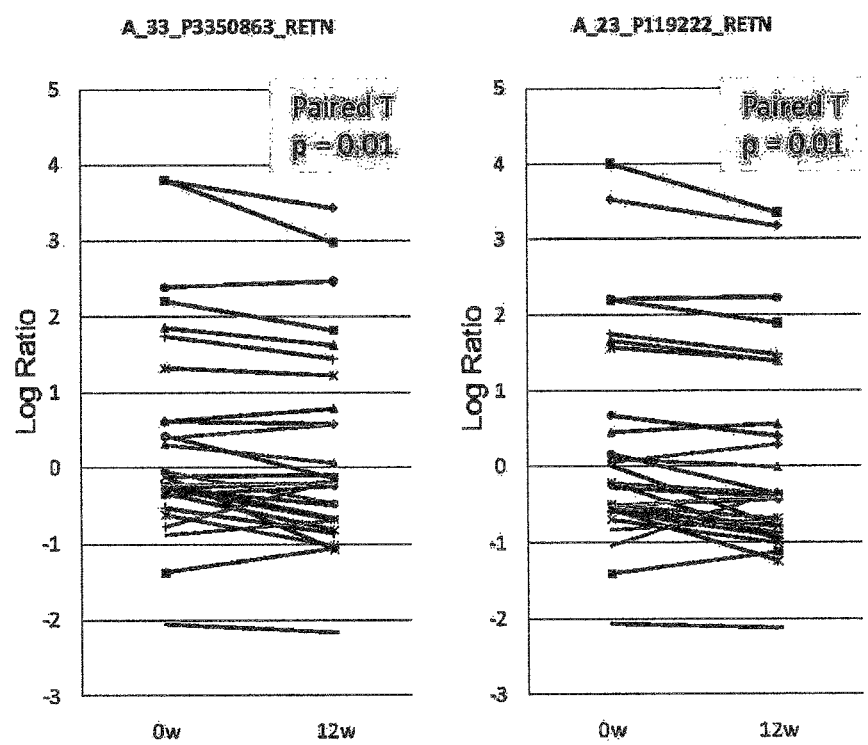
FIG. 2 is a results of measurement of two probes for resistin mRNA, i.e., A_33_P3350863 and A_23_P119222, obtained before the test period (0 w) and after the end of the test period (12 w).

The results of measurement with two probes for resistin mRNA, i.e., A_33_P3350863 and A_23_P119222, before the test period (0 w) and after the end of the test period (12 w) are shown in FIG. 2; the expression of the resistin gene was significantly suppressed with oral administration of the test substance.

Figure 3:
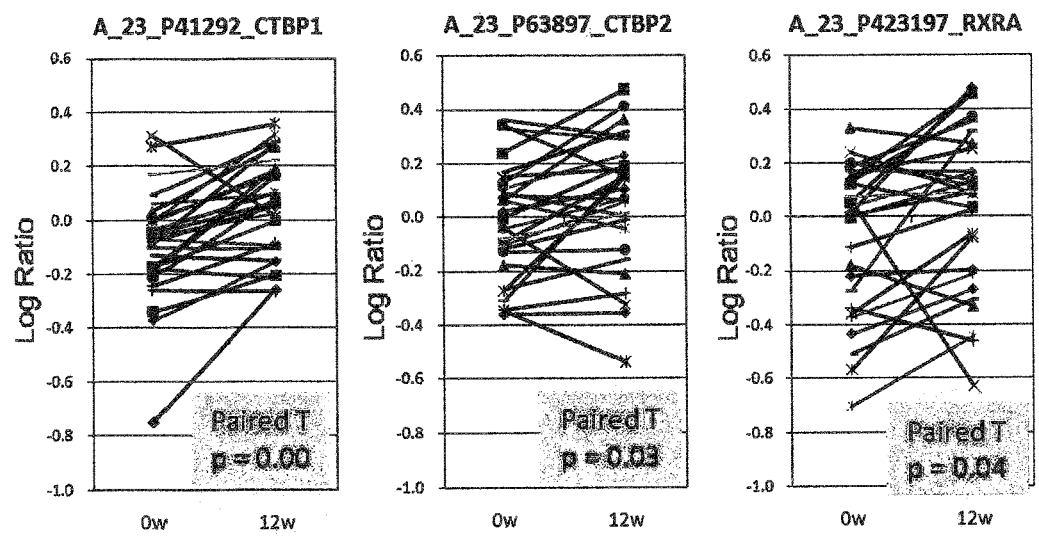
FIG. 3 is a results of measurement of the expression of the CTBP1 gene, the CTBP2 gene, and the RXR-alpha gene, which are genes that negatively control the expression of the resistin gene, obtained before the test period (0 w) and after the end of the test period (12 w).

(3) Expression of Genes that Negatively Control the Expression of the Resistin Gene The results of measurement of the expression of the CTBP1 gene, CTBP2 gene, and RXR-alpha gene, which negatively control the expression of the resistin gene, before the test period (0 w) and after the end of the test period (12 w) are shown in FIG. 3; the expression of each of the aforementioned genes that negatively control the expression of the resistin gene was significantly increased with oral administration of the test substance.

What is claimed is:

1. A method for reducing a serum resistin level in a subject in need thereof, the method comprising:
   orally administering a dosage of a serum resistin level reducing agent to the subject every day for successive 12 weeks such that the serum resistin level of the subject is reduced, wherein said serum resistin level reducing agent is prepared by a process comprising providing an aqueous suspension of *Chlorella pyrenoidosa* powder containing 10 to 25% by weight of the *Chlorella pyrenoidosa* powder;

adjusting the temperature of the aqueous suspension to no more than 10° C.;

pulverizing said *Chlorella pyrenoidosa* powder within the aqueous suspension, whereby the temperature of said aqueous suspension is warmed to no more than 40° C. during said pulverizing, to form a pulverized suspension of cell wall-disrupted *Chlorella pyrenoidosa*; and cooling said pulverized suspension to a temperature of no more than 10° C. to form said serum resistin level reducing agent;

wherein said dosage contains 1g to 35g of the cell wall-disrupted *Chlorella pyrenoidosa*.

2. The method according to claim 1 wherein the serum resistin level reducing agent reduces the expression of a resistin gene.

3. The method according to claim 1 wherein the serum resistin level reducing agent increases an expression of a CTBP1 gene.

4. The method according to claim 1 wherein the serum resistin level reducing agent increases an expression of a CTBP2 gene.

5. The method according to claim 1 wherein the serum resistin level reducing agent increases an expression of a RXR-alpha gene.

* * * * *